United States Patent [19]

Burch

[11] Patent Number: 5,433,226
[45] Date of Patent: Jul. 18, 1995

[54] DENTAL FLOSS BASED ON ROBUST SEGMENTED ELASTOMER

[75] Inventor: Robert R. Burch, New Orleans, La.

[73] Assignee: Delta Dental Hygienics, L.L.C., New Orleans, La.

[21] Appl. No.: 207,936

[22] Filed: Mar. 9, 1994

[51] Int. Cl.⁶ .............................................. A61C 15/00
[52] U.S. Cl. ................................................... 132/321
[58] Field of Search ........................... 132/321, 329

[56] References Cited

U.S. PATENT DOCUMENTS

| | | | |
|---|---|---|---|
| 2,772,205 | 11/1956 | King | 167/93 |
| 3,247,857 | 4/1966 | Kanbar | 132/93 |
| 3,789,858 | 2/1974 | Pesce | 132/321 |
| 3,800,812 | 4/1974 | Jaffe | 132/89 |
| 3,838,702 | 10/1974 | Standish | 132/89 |
| 3,896,824 | 7/1975 | Thornton | 132/321 |
| 3,943,949 | 3/1976 | Ashton et al. | 132/321 |
| 4,142,538 | 3/1979 | Thornton | 132/321 |
| 4,583,564 | 4/1986 | Finkelstein et al. | 132/321 |
| 4,836,226 | 6/1989 | Wolak | 132/321 |
| 4,974,614 | 12/1990 | Selker | 132/321 |
| 4,974,615 | 12/1990 | Doundoulakis | 132/321 |
| 5,076,300 | 12/1991 | Mayfield | 132/321 |
| 5,353,820 | 10/1994 | Suhonen et al. | 132/321 |

FOREIGN PATENT DOCUMENTS 0292673 11/1988 European Pat. Off. .

Primary Examiner—Cary E. O'Connor
Attorney, Agent, or Firm—E. Vassiliou

[57] ABSTRACT

A dental hygiene product, and more particularly dental floss comprising a fiber having a core of a segmented polymer. The segments of the polymer are a combination of soft segments, preferably of polyether or polyester type, and of hard segments selected from a group consisting of polyurethane, polyamide, polyimide, and a mixture thereof. The content in hard segments is 5–40% of the polymer by weight. The dental floss of this invention is characterized by exceptionally robust elastic properties, which are necessary to ensure effective and efficient cleaning of teeth.

23 Claims, 3 Drawing Sheets

DENTAL FLOSS BASED ON ROBUST SEGMENTED ELASTOMER

1. Field of the Invention

This invention relates to articles of dental hygiene, and more particularly to dental floss.

2. Background of the Invention

Dental floss is a very well known and broadly used article of dental hygiene. There are many benefits attributed to dental flossing, and especially daily dental flossing.

Dental flossing removes residual food particles, which cannot be removed by brushing, from in between teeth, and in general maintains the gums in good health. Thus, among other benefits, it decreases the incidence of dental caries, gingivitis, halitosis, and dysgeusia (bad taste). It may also reduce the incidence of plaque formation.

A National Survey on Oral Health of U S Employed Adults and Seniors, conducted by the U S Department of Health and Human Services, NIH Publication No. 87-2868, 1987, gives the following results:

1: Ages 18-65, 4% caries free Age 65+, 7% caries free, 59% edentulous
2: Root surface caries 21%, seniors 63%
3: Coronal caries 21%
4: Gingivitis 44-47%
5: Subgingival calculus 53-66%
6: Supragingival calculus 23-31%
7: The above statistics vary with:
  a: Age
  b: Region of the country
  c: Education
  d: Income A National survey of dental caries in U S school children 1986-87, U S Dept of Health and Human Services 1989, shows the following:

| Oral health in US children ages 5-17 | | |
|---|---|---|
| | 1979-80 | 1986-87 |
| Decayed | 16.8% | 13.4% |
| Filled | 76.1 | 83.3 |
| Missing | 7.1 | 4.3 |

The effect of using dental floss on plaque and gingivitis has also been described by Lobene et al. in "Clinical Preventive Dentistry", Vol. 4, No. 1, pp. 5-8, January-February 1982.

There are different reasons why many people do not floss with presently available dental floss. Among them:

1: Discomfort when flossing;
2: Time required to floss;
3: Difficulty in inserting floss between teeth;
4: Floss often fragments or breaks; and
5: Floss fragments lodge between teeth and are difficult to remove.

Furthermore, the spacing between teeth is not uniform, and it varies considerably not only from one place to another place between the same pair of teeth, but also from one pair of teeth to another pair of teeth. The medial 50% portion of a tooth has a greater diameter than the proximal and distal portions of that tooth. The spacing varies in the same individual, among different individuals, and especially in the case of twisted teeth. The spacing is greatest at the gum line.

The type of dental floss found extensively in the marketplace is a substantially non-elastic strand, which is cut into segments by the user. These segments are forced between teeth in order to remove plaque and foreign objects from the spaces in between teeth.

This is one of the major reasons why the non-elastic strand of dental floss, which inherently has a constant diameter, cannot perform the cleaning act effectively. For some regions of the spacing to be cleaned between one tooth and another tooth adjacent to it, the diameter of the presently used dental floss may be suitable, but in some other regions may be too small, and still for other regions may be too large.

Many attempts have been made in vein to correct this problem. Elastic or elastomeric strands have been proposed in a variety of configurations. However, none of these approaches confronted the problem successfully, since in attempting to resolve the problem of how to deal with the spacing variability, they created even more severe problems, without resolving the initial problem, anyway.

U.S. Pat. No. 3,247,857 (Kanbar) discloses a dental floss constituted by an extruded polymer ribbon, which has been stretch oriented to increase its strength and which is loosely twisted into a helix forming a hollow and compressive tube.

U.S. Pat. No. 3,800,812 (Jaffe) discloses a dental floss which is made by cutting a tape into strips of 1½ to 10 mils thickness, either before or after the tape has been stretched. The tape is made by extruding a polyester elastomer into a hot and tacky consistency having certain tensile properties when cooled, including a high degree of stretchability. The tape is subsequently stretched, after having been cooled, which results in development of substantially increased strength and desirable elastomeric properties. Abrasive particles and flavoring agents may be incorporated into the tape material or applied to the tape surface.

U.S. Pat. No. 3,838,702 (Standish et al.) discloses a dental floss having improved cleaning and polishing action obtained by coating the floss with a coating agent comprising a resilient wax, polymer, or elastomer, having embedded therein a finely divided particulate polishing agent.

U.S. Pat. No. 4,974,614 (Selker) discloses an improved dental floss comprising a first end, a central portion, and a second end, with the first and second ends having relatively increased cross-sectional dimensions relative to the central portion. The increased cross-sectional dimensions of the end portions enhance the ease and comfort of holding the floss during use. The floss may be dispensed from a continuous roll with a means of cutting the floss so that each length has relatively thickened ends. The floss may also be dispensed in convenient pre-cut lengths, each having thickened end portions and a relatively narrowed central portion.

U.S. Pat. No. 4,974,615 (Doundoulakis) discloses a filamentary article free of silk like fibers, made out of an elastomeric material for use in dental hygiene. The article is stretchable for proportionately reducing its cross section so that a sector thereof can enter between teeth. The article provides cuts along the edge, is twisted, or knotted at predetermined intervals along its length for furnishing radially directed edges or surfaces to help wipe food remnants, when longitudinally drawn through the larger interproximal openings, usually found in between teeth near the gums.

U.S. Pat. No. 5,076,300 (Mayfield) discloses a dental floss in which an inelastic strand is tightly wrapped around an elastic strand of a certain length and firmly tied at each end of the elastic strand. To remove matter from interproximal area between tightly spaced adjacent teeth, only the inelastic strand is used, while both the inelastic and elastic strands may be used to clean the interproximal area between widely spaced apart adjacent teeth.

U.S. Pat. No. 2,772,205 (King) discloses a dental floss with a higher aliphatic acyl amide of an aminocarboxylic acid compound absorbed thereon. These compounds have the unique property of inhibiting acid production in the mouth for a prolonged period of time.

European Patent Application 0 292 673 A2 discloses an elastic dental floss, such as a rubber band, for cleaning contact points between teeth and interdental spaces, which contains an annular extensible and contractible elastic member. The elastic member is normally stored in a contracted state and brought to an extended state at any time of cleaning the contact points and the interdental spaces. The elastic member, when in the extended state, has a cross-sectional dimension suited to clean the contact points and the interdental space and elastify sufficiently not to injure teeth, periodontal ligament and tooth gum.

None of the above references discloses, implies, or suggests the critical point of the present invention which pertains to a dental floss comprising a fiber having a core of a segmented polymer having soft segments and hard urethane segments.

3. Summary of the Invention

The instant invention is directed to articles of dental hygiene, such as dental floss for example. More particularly, the present invention pertains to a dental hygiene article comprising a fiber having a core of a segmented polymer, the polymer having soft segments and hard segments selected from a group consisting of urethane, amide, imide, and a mixture thereof. Urethane hard segments are, however, highly preferable.

The core of the fiber has preferably a content of hard segment of 5–40% by weight, while the soft segments are preferably selected from a group consisting of polyester, polyether, and a mixture thereof.

The structure of the core of the fiber is preferably selected from a group consisting of primary monofilament, primary multifilament, primary coalesced monofilament, and a combination thereof. The core of the fiber may be uncovered or bare core, core covered with a secondary filament, or a combination thereof.

The secondary filament may be a secondary monofilament, secondary multifilament, spun filament, or a combination thereof.

The fiber may also comprise abrasive matter included within the fiber, on the surface of the fiber, or a combination thereof. The fiber may also be in the form of a continuous strand, or a strand cut into adequately long pieces for flossing the teeth of a person.

The dental floss strand of the present invention may comprise an elastomeric fiber, with or without urethane, amide, or imide moieties, having
  a denier value in the range of 40–4,000, preferably in the range of 200–2,500, and more preferably in the range of 800–2,400;
  a tensile strength higher than 0.5 grams per denier; and
  a break elongation of at least 200%, and preferably of at least 300%;
the fiber requiring a stress to elongate selected from the range-group consisting of
  the range of 0.03 to 0.40 grams per denier in order to develop an elongation of 200%, and
  the range of 0.07 to 0.60 grams per denier in order to develop an elongation of 300%.

The dental floss or strand or fiber of the present invention may be assembled in a dispensing box, in a manner that the fiber is at least partially enclosed in the box for purposes of cleanliness and convenience. The fiber may also be assembled in combination with a dental instrument, so that the fiber is supported by the dental instrument in a manner to facilitate flossing of a person's teeth.

4. Description of the Drawing

The reader's understanding of the present invention will be enhanced by reference to the following detailed description taken in conjunction with the drawing figures, wherein.

5. Detailed Description of the Invention

As aforementioned, the instant invention is directed to dental hygiene; products and more particularly to a dental floss comprising a fiber having a core of a segmented polymer, the polymer having soft segments and hard urethane segments. This polymer configuration results in a fiber of very robust structure suitable for dental floss, as Applicant has discovered.

As indicated earlier in this discussion, the conventional strand of dental floss, which inherently has a constant diameter, cannot perform the cleaning act effectively. For some regions of the spacing to be cleaned between one tooth and another tooth adjacent to it, the diameter of the presently used dental floss may be suitable, but in some other regions may be too small, and still for other regions may be too large.

The spacing between teeth is not uniform, and it varies considerably not only from one place to another within the same pair of teeth, but also from one pair of teeth to another pair of teeth, which makes the problem even more severe. As it has also been aforementioned, many attempts have been made in vein to correct this problem,, especially by using elastic or elastomeric strands in a variety of configurations.

The motive behind most of these unsuccessful attempts has been to introduce a strand of variable diameter in order to accommodate and clean the spacings of different dimensions in between teeth. Thus, elastic strands were proposed, among other types of strands, since upon stretching the diameter of an elastic strand decreases as the stretched length increases. One of the biggest problems that was created by the use of elastic strands of conventional type as dental floss, was the weakness of the proposed floss resulting in premature failure and in not performing the function which it was supposed to perform.

Natural rubber, as well as artificial rubbers, are weak in the very small diameters which are necessary in the case of dental floss. Thus, although the diameter of a rubbery or elastic or elastomeric material is variable with stretching, the low tensile strength and the excessively high elongation observed with relatively little force, make these dental flosses, which are based on conventional elastic strands, impractical.

Applicant has now discovered that there is one type of elastomeric material, called robust elastomer for the purposes of the present invention, which does not have these pitfalls, and it may be used in the construction of practically effective and efficient dental floss.

The robust elastomer of the present invention, as already mentioned hereinabove, and as it will be explained in detail hereinbelow, is a polymer having soft segments, preferably of polyester or polyether, and hard segments of urethane, or amide, or imide, or a mixture thereof. The content in hard segments is preferably in the range of 5–40% by weight of the total polymer, and more preferably in the range of 15–25% by weight of the total polymer. The content of the soft segment is preferably in the range of 60–95% by weight of the total polymer, and more preferably in the range of 75–85% by weight of the total polymer.

Examples of polymers which are suitable for the purposes of the present invention are polymers having the generic name "Spandex". A good review of Spandex elastomeric fibers is given by L. Rose in the Reprints, Progress in Applied Chemistry (London), Vol. 51, p. 609, 1966.

Meredith and Fyfe in Text. inst. Ind., Vol. 2, p. 154, 1964, and Bamford in Text. Inst. Ind., Vol. 55, p. 73, 1965, discuss the structural aspects of Spandex, and give suggestions about its elastomeric properties. The soft segments in the case of Spandex, which are preferably polyethers, polyesters, or a combination thereof, have preferably low internal cohesion, and they are analogous to the hydrocarbon chains in the case of natural rubber. The hard segments of preferably aromatic polyurea are linked occasionally to the soft segments through urethane bonds, and they are analogous to the covalent sulfide bonds of vulcanized rubber.

U.S. Pat. Nos. 2,692,873, 2,751,363, 2,751,419, 3,061,574, 3,071,557, 3,133,036, and 3,149,998, British Patents 934,519 and 1,040,055, as well as Canadian Patent 692,058, all ten of which are incorporated herein by reference, give examples of making Spandex compositions and fibers.

An example of a series of commercial products, which are suitable for the ;practice of the instant invention, and which come under the registered name LYCRA ®, are available from DuPont, Wilmington, Del. The structure and properties of LYCRA ® are briefly discussed by Hicks in the American Dyestuff Reporter, pp. 33–35, Jan. 7, 1963. A number of bulletins describing different aspects of LYCRA ® are also available from DuPont.

Important properties of LYCRA ® or other Spandex fibers include, but not: limited to:
 1. Outstanding tensile strength as compared to natural or other synthetic rubbers or elastomeric materials;
 2. Diameter decreases with stretch;
 3. Percent decrease in diameter related to the degree of stretch;
 4. Returns to original diameter with release of stretch;
 5. Diameter not increased with wetting;
 6. Water acts as lubricant;
 7. Durable over time without loss of properties; and
 8. Excellent cut-resistance
 9. Inexpensive The advantages of LYCRA ® or other Spandex fibers as a dental floss include, but not limited to:
 1. Easy and safe to use
   a. The variable diameter with stretch enables use in variable teeth spacing,
   b. Because of its good tensile strength, it does not break easily, as compared to rubber dental flosses as referenced above, which are prone to break easily and injure the gums of the dental floss user,
   c. In contrast to rubber floss, it does not become brittle with time, thus avoiding premature breaking due to aging and gum injury during flossing, and
   d. Once wrapped around the index finger for use, the stretch release anchors the Spandex fiber with less chance of slipping, when compared to regular floss;
   e. Considerably more comfortable to the gums;
 2. Its wet smooth surface avoids gum injury;
 3. It is hypo-allergenic, and it does not have the tackiness, stickiness and unpleasant odor of rubber;
 4. It is inexpensive;
 5. It is believed by Applicant to be in general more conducive to widespread flossing as compared to flossing with either non-elastic elastic or rubber made dental floss; and
 6. In contrast to rubber, it does not become brittle with time as aforementioned, so it may be stored for indefinite periods of time.
 7. It is readily available in a variety of deniers to accommodate various interdental spacings.

Figure 1:
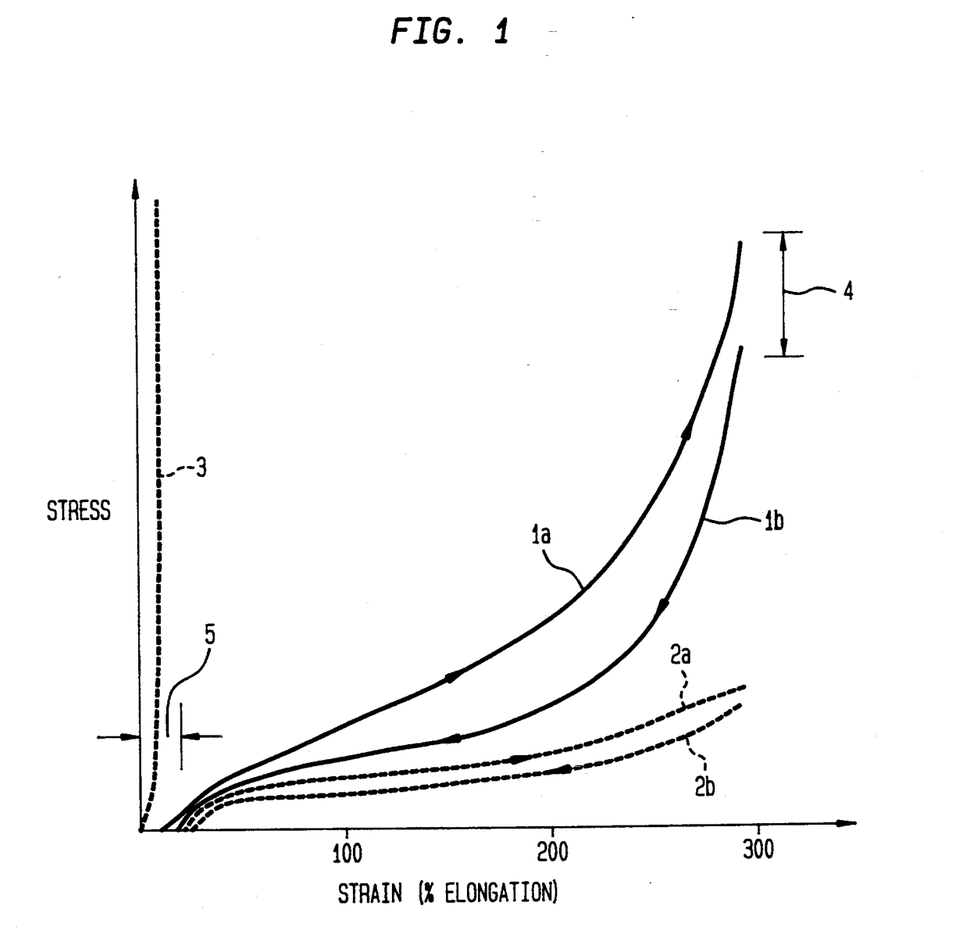
FIG. 1 is a schematic diagram illustrating the stress-strain behavior of conventional non-elastic dental floss, a rubber dental floss, and dental floss according to the present invention.

Referring now to FIG. 1, there is depicted a schematic diagram, in arbitrary stress units, illustrating the behavior of a Spandex fiber as compared to the behavior of natural rubber, and of a conventional non-elastic fiber, with regard to strain vs. stress.

A strand or fiber made out of natural rubber follows the path 2a during a stretching period (as the stress is being increased), while it follows the path of curve 2b during a release period (as the stress is being decreased). In the same manner, a LYCRA ® fiber follows the path 1a during a stretching period, while it follows the path of curve 1b during a release period. A non-elastic fiber, such as Nylon for example, follows the path of curve 3. In the case of the non-elastic fiber, the curves followed by stretching and releasing are too close to each other to be shown in FIG. 1, so that they are represented by the single curve 3.

A stress decay 4 in the case of LYCRA ® is observed at an elongation of 300%, while a set value of 5 is observed at the beginning of stretching.

One may realize immediately the large difference shown in the stress-strain behavior of the three classes of fibers.

The non-elastic fiber, following the path of curve 3, is too rigid to serve the purposes of the present invention. At the other end, the rubber fiber, following the path of curves 2a and 2b is too sluggish, and therefore, also unsuitable for the purposes of this invention. Finally, the Spandex fiber following the path of curves 1a and 1b, is robust enough to serve; the purposes of this invention. As shown in FIG. 1, the Spandex fiber is adequately elastic to reversibly stretch when subjected to a stress, but the stress required for further stretching increases considsrably with elongations in the range of 200 to 400%. This, combined with the rather high tensile strength as compared to other elastomers, gives the Spandex fiber the robust behavior needed for its use as dental floss according to this invention.

In the context of the present invention, other than Spandex-type elastomeric fibers may also be used as long as among other requirements, such as for example denier value, texture, smoothness and the like, they fulfill three very important criteria.

The first is for the fiber to have a tensile strength of more than 0.5 grams per denier, preferably more than 0.65 grams per denier, and even more, preferably more than 0.75 grams per denier.

The second is for the fiber to require a stress of either
in the range of 0.03 to 0.40 grams per denier, more preferably in the range of 0.04 to 0.25 grams per denier, and even more preferably in the range of 0.04 to 0.20 grams per denier in order to develop an elongation of 200%, or in the range of 0.07 to 0.60 grams per denier, more preferably in the range of 0.08 to 0.50 grams per denier, and even more preferably in the range of 0.09 to 0.30 grams per denier in order to develop an elongation of 300%.

The third is for the fiber to have a break elongation of at least 200%, and more preferably at least 300%; that is the fiber not to break before it elongates at least to that degree.

In addition to the above three criteria, the fiber should preferably be stable with age. Preferably, the fiber should not lose more than 20% of its original tensile strength in one year, and more preferably it should lose not more than 10% per year.

The preferable denier value of the Spandex, such as LYCRA ® for example, or other elastomeric fiber according to this invention should be in the range of 40 to 4,000, more preferably in the range of 200 to 2,500, and even more preferably in the range of 800 to 2,400.

As aforementioned, a dental hygiene article, which may be in the form of dental floss, comprises a fiber having a core of a segmented polymer, which polymer has soft segments and hard segments selected from the group consisting of urethane, amide, imide, and a mixture thereof. Preferably the content of the polymer in hard segments should be in the range of 5–40% by weight, with the rest being polyether or polyester or a mixture of polyether and polyester segments. The terms "urethane", "amide", "imide", include of course "polyurethane", "polyamide", and "polyimide". Similarly, the terms "polyether", and "polyester"0 include monoether and monoester moieties. It is important that the, different segments are bound together with chemical bonds in the polymer.

Figure 2:
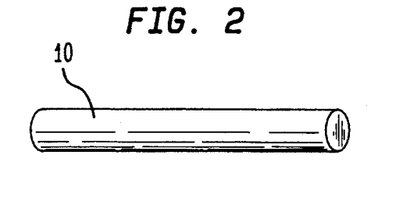
FIG. 2 is a schematic diagram illustrating a portion of a core of a dental floss fiber according to one embodiment of the present invention.

The core of the fiber which is comprised in the dental hygiene article, which item may be dental floss, may be a primary monofilament as better shown in FIG. 2. FIG. 2 shows schematically just a portion of a primary monofilament for purposes of clarity. The primary monofilament 10 may have a round cross-section as shown in FIG. 2, which constitutes the preferable configuration. However, the cross section may have any other shape, such as for example square, rectangular, polygonal, irregular, and the like. The diameter of the primary monofilament may also be variable.

Figure 3:
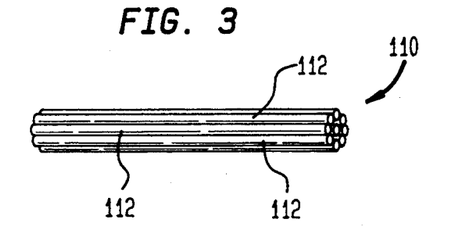
FIG. 3 is a schematic diagram illustrating a portion of a core of a dental floss fiber according to another embodiment of the present invention.

The core of the fiber may also be in the form of primary multifilament 110, as better shown in FIG. 3, comprising a multiplicity of monofilaments 112. The monofilaments 112 may be woven together, twisted, and in general formed in any conventional manner that fibers are manufactured. Further, the monofilaments 112 may be coalesced into one primary coalesced monofilament, somewhat similar to the primary multifilament 11 0, with the difference that the monofilaments 112 have been fused together to a desired degree, at least at the contact regions of the monofilaments, to form the unitary primary coalesced monofilament.

Figure 4:
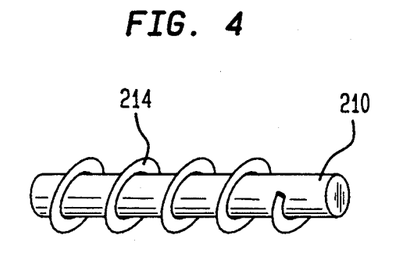
FIG. 4 is a schematic diagram illustrating a portion of a core of a dental floss fiber covered with a secondary filament according to a different embodiment of the present invention.
Figure 5:
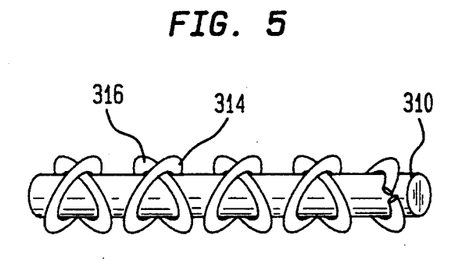
FIG. 5 is a schematic diagram illustrating a portion of a core of a dental floss fiber covered with two secondary filaments according to another embodiment of the present invention.

The core may be bare or covered partially or totally with a secondary monofilament or polyfilament. The core 210 may be covered by a single secondary mono- or multi-filament 214, as better shown in FIG. 4. It may also be covered by more than one secondary mono- or multifilament. In FIG. 5, the core 310 is covered by two secondary mono- or multi-filaments 314 and 316, which are twisted in opposite helical directions, in the case of FIG. 5. In addition, the core 410, as better shown in FIG. 6, may be covered by a secondary spun filament 414.

The secondary filaments may be any conventional fibers, elastomeric or non-elastic. Examples include, but are not limited to, nylon, acrylic, acetate, cotton, wool, polyester, LYCRA ®, other natural or synthetic fibers, and the like.

Figure 6:
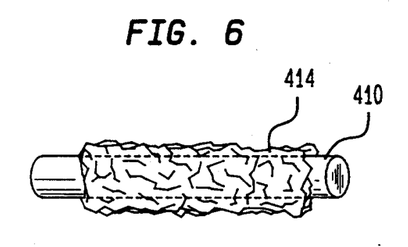
FIG. 6 is a schematic diagram illustrating a portion of a core of a dental floss fiber covered with spun filament according to still another embodiment of the present invention.

The dental floss fiber of the present invention may comprise abrasive matter for better cleaning of the teeth. The abrasive matter may be incorporated into any part of the body of the fiber, such as for example the primary or secondary filaments or both. It may also be incorporated on the surface of any or all the primary or secondary filaments, by any well known to the art techniques. In the case of the core .410 surrounded by spun filament 414, as shown in FIG. 6, the abrasive matter may be trapped within the fibrils of spun filament 414.

When the abrasive matter is incorporated in the body of the filaments, and especially filaments of the core, care should be taken not to overfill the filament with abrasive matter to the point that it loses its strength and elasticity. Any conventional polishing matter, used for example for polishing teeth, may be employed as an abrasive matter for the purposes of the present invention. This includes, but is not limited to appropriate oxides, such as aluminum oxide and silicon dioxide for example, silicates, carbonates, phosphates, and the like. Preferable materials are pumice, talc, calcium silicate, calcium carbonate, and zirconium oxide.

The average particle size is preferably lower than 50 micrometers, and more preferably in the range of 1 to 15 micrometers.

The abrasive or polishing matter may be incorporated to the surface of one or more primary or secondary filaments by coating such filaments with a matrix containing the polishing matter, by well known to the art methods. Such matrices include but are not limited to waxes, polyethylene, polybutadiene, elastomers, acrylic or methacrylic based polymers, polyurethanes, and the like. U.S. Pat. No. 3,838,702, which is incorporated herein by reference, describes miscellaneous polishing agents, matrices containing such agents for coating dental floss, and methods of applying the matrices on dental floss.

The dental floss of the instant invention may also comprise ingredients which increase the resistance of teeth to dental caries. For example, U.S. Pat. Nos. 2,667,443, 2,772,205, and 5,280,796, all of which are incorporated herein by reference, describe such ingredients and methods of applying them on dental floss.

The floss of this invention may be in the form of a continuous strand or in pieces of a desired length. The floss should preferably be maintained in a box, where it should be at least partially enclosed. Such boxes containing dental floss are very well known to the art, and they usually have means for the user to cut a continuous strand to any desired length.

Figure 7:
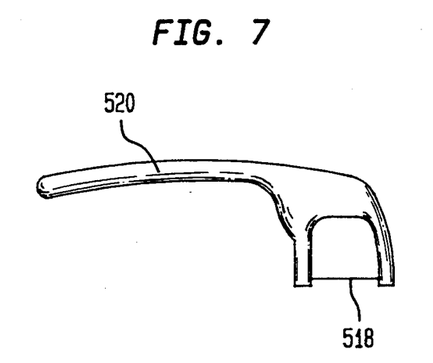
FIG. 7 is a schematic diagram of dental floss supported on a dental instrument according to an alternate embodiment of this invention.

In a different embodiment, better shown in FIG. 7, the dental floss 518 of this invention is assembled in a dental instrument 520 for better handling and easier flossing. The dental instrument 520 is preferably disposable and made of plastic material. Other types of dental instruments are exemplified in U.S. Pat. Nos. 3,236,247, 5,010,906, 5,267,579, and 5,280,797, which are incorporated herein by reference.

It should be understood that any combination of the above configurations may be used to form the dental floss fiber or strand of the present invention.

Figure 8:
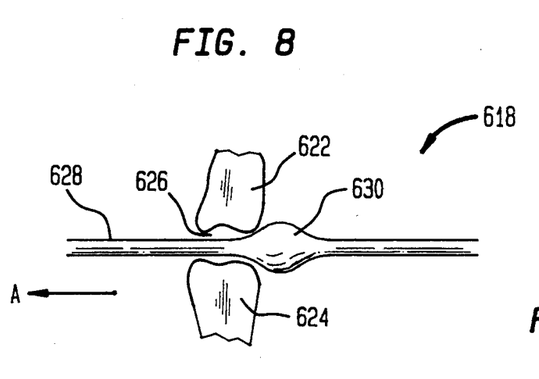
FIG. 8 is a schematic diagram illustrating one aspect of the operation of the floss of the present invention.

In operation of the embodiments of the present invention, better shown in FIG. 8, the user of the dental floss, stretches the fiber 618 to a desired degree and forces it through two adjacent teeth 622 and 624, having a spacing 626 to be cleaned. In sequence, the user reciprocates the floss of this invention back and forth. During this movement, for example in the direction indicated by the arrow A, the front part 628 of the floss is stretched and develops a small diameter, easily passing through the spacing 626. The back part 630 of the floss or fiber 618 maintains at least the original unstretched diameter and as it passes through the spacing 626, it cleans it thoroughly. When the floss 618 is forced to move in a direction opposite to the one indicated by the arrow A, the former front part 628 becomes now a back part, maintaining at least the unstretched diameter, thus continuing to clean thoroughly the spacing 626 from the other side. After thorough cleaning has been achieved, the user removes the floss 618 from the spacing in between teeth 622 and 624, in order to clean a spacing of another pair of teeth.

Figure 9:
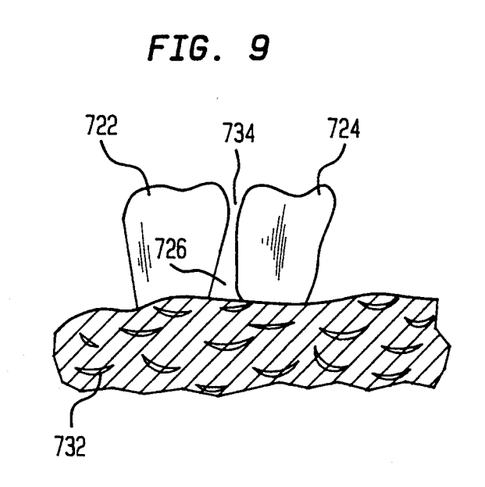
FIG. 9 is a schematic diagram illustrating a pair of teeth, with upper and lower spacings in between the teeth.

It should be pointed out that, as better shown in FIG. 9, since the dental floss of the present invention has variable diameter, it can pass easily through the upper spacing 734 between teeth 722 and 724, and still have adequately large diameter to clean the lower spacing 726 close to the gum 732, as described hereinabove. The well controlled stretchability combined with high tensile strength, among other attributes, as discussed hereinabove, make fibers having the behavior of Spandex, outstanding material for use as dental floss.

Non-elastic fibers in order to pass through the upper spacing 734, have to have an accordingly small diameter, and therefore they cannot clean the lower spacing 726 thoroughly. Dental flosses made of rubber or other elastomers referred to in the art so far, present excessive stretchability with unacceptably low tensile strength to serve the purposes of the present invention. They break easily with potential injury of the user, and they also present all the disadvantages, already discussed.

Figure 10:
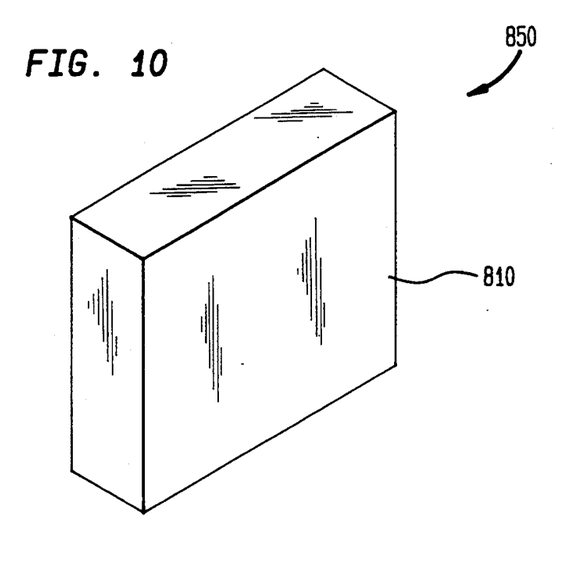
FIG. 10 is a schematic diagram illustrating a dispensing box in which the fiber or strand of the present invention is at least partially enclosed.

As aforementioned, the floss 810 of this invention should preferably be at least partially enclosed in a box 850, better shown in FIG. 10. Such boxes containing dental floss are very well known to the art, and they usually have means for the user to cut a continuous strand to any desired length.

Applicant tested a number of different available dental floss versions, and compared them with LYCRA ® as dental floss, using a rating of 0 to 10, 0 being the worst overall and 10 the best overall, with the following results:

1: Brand, 1, plain or minted
  Rigid, poor for tight spaces, difficult to get between teeth or to remove, has a thick and thin end; above applies to both ends; mint flavor tastes good.
  Rating: 5-6
2: Brand 2, nylon waxed, multiple strands
  $0.99 per 100 yards; difficult to insert between tight teeth and to remove; strands break.
  Rating: 7-8
3: Brand 3, unwaxed, multiple strands
  $1.19 per 50 yards; difficult to use between tight teeth; nicely packed
  Rating: 5-6
4: Brand 4, extra fine, unwaxed, multiple strands
  $1.19 per 50 yards; not much thinner than no. 3 above; strands break easily; difficult to use between tight teeth
  Rating: 7-8
5: Brand 5, waxed, multiple strands, probably nylon.
  $3.25 per 200 yds; difficult to use between tight teeth; strands break
  Rating: 8-8.5
6: Brand 6, unwaxed, multiple strands, probably nylon
  $2.49 per 50 cuts; thin and thick ends; thin end difficult to insert between tight teeth; thick end surface is frayed.
  Rating: 5-6
7: Brand 7, unwaxed, multiple strands
  Difficult to insert between tight teeth; strands break easily.
  Rating: 5-6

All of the above non-elastomeric floss-products were difficult to anchor around the finger.

LYCRA ®
1: Denier 22.40
  Thick, strong, excellent for spaced teeth; too thick for most of my teeth
  Rating: 9
2: Denier 1680
  Excellent, easy to use, strong; slightly tight with close teeth but with additional stretch inserts and removes with little effort.
  Rating: 9-10
3: Denier 840
  Excellent strength, easy to insert and remove; best for my teeth Rating: 10
4: Denier 280
Very thin, breaks easily; good for tight teeth spacing, but it breaks some times in use.
Rating: 8–9

The above examples have been given for demonstration purposes only and should not be construed as limiting the scope of the present invention. Also, the embodiments described hereinabove have only been given to better clarify the present invention, and they should not be taken in a manner limiting the breadth of the claimed matter.

The different aspects of the present invention, exemplified by the various aforegiven embodiments, may be used as described, but also after any modifications or in any combination resulting thereof.

In the figures of the drawing, as well as in the description of the present invention, numbers differing by 100 represent similar elements having similar functions.

What is claimed is:

1. A dental hygiene article comprising a fiber having a core of a segmented polymer, the polymer having soft segments and hard segments selected from a group consisting of urethane, amide, imide, and a mixture thereof, the hard segments being linked occasionally to the soft segments by covalent bonds.

2. A dental hygiene article as defined in claim 1, wherein said article is a dental floss.

3. A dental hygiene article as defined in claim 2, wherein the core of the fiber is selected from a group consisting of primary monofilament, primary multifilament, primary coalesced monofilament, and a combination thereof.

4. A dental hygiene article as defined in claim 2, wherein the core of the fiber is selected from a group consisting of uncovered core, core covered with a secondary filament, and a combination thereof.

5. A dental hygiene article as defined in claim 4, wherein the secondary filament is selected from a group consisting of secondary monofilament, secondary multifilament, spun filament, and a combination thereof.

6. A dental hygiene article as defined in claim 4, wherein the fiber comprises abrasive matter in a form selected from a group consisting of inclusion of the abrasive matter within the fiber, coating the abrasive matter on the surface of the fiber, and a combination thereof.

7. A dental hygiene article as defined in claim 4, wherein the fiber is in the form selected from a group consisting of continuous strand and strand cut into adequately long pieces for flossing the teeth of a person.

8. A dental hygiene article comprising a fiber having a core of a segmented polymer, the polymer having soft segments and hard segments selected from a group consisting of urethane, amide, imide, and a mixture thereof, the hard segments being present in the range of 5–40% by weight.

9. A dental floss comprising a fiber having a core of a segmented polymer, the polymer having soft segments and hard segments selected from a group consisting of urethane, amide, imide, and a mixture thereof, the hard segments being present in the range of 5–40% by weight.

10. A dental floss comprising a fiber having a core of a segmented polymer, the polymer having soft segments selected from a group consisting of polyester, polyether, and a mixture thereof and hard segments selected from a group consisting of urethane, amide, imide, and a mixture thereof.

11. An assembly of a box and a dental floss at least partially enclosed in said box, the dental floss comprising a fiber having a core of a segmented polymer, the polymer having soft segments and hard segments selected from a group consisting of urethane, amide, imide, and a mixture thereof, the content of the core in hard segment being in the range of 5–40%.

12. An assembly as defined in claim 11, wherein the core of the fiber is selected from a group consisting of primary monofilament, primary multifilament, primary coalesced monofilament, and a combination thereof.

13. An assembly as defined in claim 11, wherein the core of the fiber is selected from a group consisting of uncovered core, core covered with a secondary filament, and a combination thereof.

14. An assembly as defined in claim 13, wherein the secondary filament is selected from a group consisting of secondary monofilament, secondary multifilament, spun filament, and a combination thereof.

15. An assembly as defined in claim 13, wherein the fiber comprises abrasive matter in a form selected from a group consisting of inclusion of the abrasive matter within the fiber, coating the abrasive matter on the surface of the fiber, and a combination thereof.

16. An assembly as defined in claim 13, wherein the fiber is in the form selected from a group consisting of continuous strand and strand cut into adequately long pieces for flossing the teeth of a person.

17. An assembly of a dental instrument and a fiber supported on said instrument in a manner to allow flossing of a person's teeth, the fiber having a core of a segmented polymer having soft segments and hard segments selected from a group consisting of urethane, amide, imide, and a mixture thereof, the content of the core in hard segment being in the range of 5–40% by weight.

18. An assembly as defined in claim 17, wherein the core of the fiber is selected from a group consisting of primary monofilament, primary multifilament, primary coalesced monofilament, and a combination thereof.

19. An assembly as defined in claim 17, wherein the core of the fiber is selected from a group consisting of uncovered core, core covered with a secondary filament, and a combination thereof.

20. An assembly as defined in claim 19, wherein the secondary filament is selected from a group consisting secondary monofilament, secondary multifilament, spun filament, and a combination thereof.

21. An assembly as defined in claim 19, wherein the fiber comprises abrasive matter in a form selected from a group consisting of inclusion of the abrasive matter within the fiber, coating the abrasive matter on the surface of the fiber, and a combination thereof.

22. A dental floss strand comprising an elastomeric fiber having
   a denier value in the range of 40 to 4,000;
   a tensile strength higher than 0.5 grams per denier; and
   a break elongation of at least 400%;
the fiber requiring a stress to elongate selected from the range group consisting of
   the range of 0.03 to 0.40 grams per denier in order to develop an elongation of 200%, and
   the range of 0.07 to 0.60 grams per denier in order to develop an elongation of 300%.

23. A dental hygiene article comprising a fiber having a core of a segmented polymer, the polymer having soft segments and hard segments, wherein the hard segments consist substantially of urethane, and the soft segments are selected from a group consisting of polyether and polyester in an amount of 75–85% by weight of the segmented polymer.

* * * * *

UNITED STATES PATENT AND TRADEMARK OFFICE
CERTIFICATE OF CORRECTION

PATENT NO. : 5,433,226
DATED : July 18, 1995
INVENTOR(S) : Robert R. Burch

It is certified that error appears in the above-indentified patent and that said Letters Patent is hereby corrected as shown below:

Column 10, line 57, "22.40" should read --2240--

Signed and Sealed this

Twelfth Day of December, 1995

Attest:

BRUCE LEHMAN

*Attesting Officer*   *Commissioner of Patents and Trademarks*